(12) United States Patent
Zubieta et al.

(10) Patent No.: US 12,077,767 B2
(45) Date of Patent: Sep. 3, 2024

(54) ALTERING THERMORESPONSIVE GROWTH IN PLANTS VIA GENOME EDITING OF PHYTOCHROME INTERACTING FACTOR 4 (PIF4) REGULATORY ELEMENTS

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR)

(72) Inventors: Chloé Zubieta, Grenoble (FR); Aditya Nayak, Grenoble (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 0 days.

(21) Appl. No.: 16/820,838

(22) Filed: Mar. 17, 2020

(65) Prior Publication Data
US 2020/0299713 A1  Sep. 24, 2020

(30) Foreign Application Priority Data
Mar. 18, 2019 (EP) .................................. 19305324

(51) Int. Cl.
C12N 15/82 (2006.01)
(52) U.S. Cl.
CPC ..... *C12N 15/8271* (2013.01); *C12N 15/8213* (2013.01); *C12N 15/8218* (2013.01)
(58) Field of Classification Search
CPC ............................ C12N 15/8271; C12N 15/82
See application file for complete search history.

(56) References Cited

U.S. PATENT DOCUMENTS

2019/0071717 A1* 3/2019 Zhang ...................... C12N 9/22

FOREIGN PATENT DOCUMENTS

WO  WO 2011/083290  7/2011

OTHER PUBLICATIONS

Joseph Ecker, SALKseq_132713.0, https://www.arabidopsis.org/servlets/TairObject?type=polyallele&name=SALKseq_132713.0, Nov. 10, 2017 (Year: 2017).*
Arabidopsis Gene Regulatory Information Server, https://agris-knowledgebase.org/AtcisDB/atcisview.html?id=At2g43010 Binding Sites in upstream region of At2g43010, 2012 (Year: 2012).*
Sequences flanking the hexameric G-box core CACGTG affect the specificity of protein binding. M E Williams, R Foster, N H Chua The Plant Cell Apr. 1992, 4 (4) 485-496; DOI: 10.1105/tpc.4.4.485 (Year: 1992).*
Organization and cell differentiation in lateral roots of *Arabidopsis thaliana* J.E. Malamy, P.N. Benfey Development 1997 124: 33-44; (Year: 1997).*
Joseph Ecker, SALKseq_132713.0, https://www.arabidopsis.org/servlets/TairObject?id=6007229&type=global_assignment, Nov. 10, 2017 (Year: 2017).*
Ibáñez Robles, Regulation of phenotypic plasticity in high ambient temperature: ELF3 and BZR1 as major thermostats gating PIF4 signaling, Martin Luther University, 201 (Year: 2017).*
Boudreau, Diane, et al. "Crops | National Geographic Society." Education.nationalgeographic.org, National Geographic, May 13, 2022, education.nationalgeographic.org/resource/crop/. (Year: 2022).*
"Dicotyledon." Encyclopædia Britannica, Encyclopædia Britannica, inc., www.britannica.com/plant/dicotyledon. Accessed Jan. 11, 2024. (Year: 2024).*
Pucker, Boas, Nils Kleinbölting, and Bernd Weisshaar. "Large scale genomic rearrangements in selected *Arabidopsis thaliana* T-DNA lines are caused by T-DNA insertion mutagenesis." BMC genomics 22.1 (2021): 1-21. (Year: 2021).*
Wei, Kaifa, and Huiqin Chen. "Comparative functional genomics analysis of bHLH gene family in rice, maize and wheat." BMC plant biology 18 (2018): 1-21. (Year: 2018).*
Wei, Kaifa, and Huiqin Chen. "Comparative functional genomics analysis of bHLH gene family in rice, maize and wheat. Supplmental Figure 2" BMC plant biology 18 (2018): 1-21. (Year: 2018).*
Bent, Andrew. "*Arabidopsis thaliana* floral dip transformation method." Agrobacterium protocols (2006): 87-104. (Year: 2006).*
Kumar, Transcription factor PIF4 controls the thermosensory activation of flowering, Nature, Apr. 12, 2012 (Year: 2012).*
Donald, Mutation of either G box of I box sequences profoundly affects expression from the *Arabidopsis* rbcS-1A promoter, The Embo Journal, pp. 1717-1726, 1990 (Year: 1990).*
Gangappa, S. N. et al. "PIF4 Coordinates Thermosensory Growth and Immunity in *Arabidopsis*" Current Biology, Jan. 23, 2017, pp. 243-249, vol. 27.
Huq, E. et al. "PIF4, a phytochrome-interacting bHLH factor, functions as a negative regulator of phytochrome B signaling in *Arabidopsis*" The EMBO Journal, 2002, pp. 2441-2450, vol. 21, No. 10.
Jung, J.-H. et al. "Phytochromes function as thermosensors in *Arabidopsis*" Science, Nov. 18, 2016, pp. 886-889, vol. 354, vol. 6314,.
Koini, M. A. et al. "High Temperature-Mediated Adaptations in Plant Architecture Require the bHLH Transcription Factor PIF4" Current Biology, Mar. 10, 2009, pp. 408-413, vol. 19.
Stavang, J. A. et al. "Hormonal regulation of temperature-induced growth in *Arabidopsis*" The Plant Journal, 2009, pp. 589-601, vol. 60.
European Search Report in European Application No. EP 19305324. 6, Jul. 30, 2019, pp. 1-8.

* cited by examiner

*Primary Examiner* — Weihua Fan
*Assistant Examiner* — Brian James Sullivan
(74) *Attorney, Agent, or Firm* — SALIWANCHIK, LLOYD & EISENSCHENK

(57) ABSTRACT

The present invention relates to a genetically engineered plant in which the G-box motif has been inactivated, thereby inhibiting the thermosensory response, and methods for preparing such a plant.

17 Claims, 3 Drawing Sheets
(3 of 3 Drawing Sheet(s) Filed in Color)

Specification includes a Sequence Listing.

ALTERING THERMORESPONSIVE GROWTH IN PLANTS VIA GENOME EDITING OF PHYTOCHROME INTERACTING FACTOR 4 (PIF4) REGULATORY ELEMENTS

The Sequence Listing for this application is labeled "Seq-List.txt" which was created on Feb. 5, 2020 and is 3 KB. The entire content of the sequence listing is incorporated herein by reference in its entirety.

FIELD OF THE INVENTION

The invention relates to a plant that is thermotolerant and to methods for promoting temperature tolerance in plants.

BACKGROUND OF THE INVENTION

Current climate change has already altered global plant phenology and projected increases in temperature pose a significant challenge to agriculture. During their life cycle, plants, as sessile organisms, are particularly at risk for exposure to environmental stresses such as changes in ambient temperature. It has been shown that every 1° C. increase in global temperature causes crop yields to decrease by 6.0% for wheat, 3.2% for rice, by 7.4% for maize and by 3.1% for soybean (Zhao et al., 2017, Proc. Natl. Acad. Sci. 114, 9326-9331).

Plants respond to changes in ambient temperature by adjusting their growth and development to optimize survival and fitness, which is mediated by sophisticated signaling networks that integrate multiple environmental and endogenous signals. Small differences in temperatures can strongly affect the plant, eventually causing cellular metabolic imbalance, elongation of hypocotyls and petioles, fewer leaves at time of flowering and decreased leaf area, accelerated transition from vegetative to reproductive growth phases, fewer seeds and smaller seed pods, and eventually lead to death.

In the face of rapid climate change, specifically increased ambient temperatures, tuning plant thermoresponse is urgently needed to engineer plants for adaptation to climate change and for securing future food production, particularly plants that are tolerant to temperature increase.

Growing evidence indicates that PIF4, a basic-helix-loop-helix (bHLH) transcription factor, acts as a molecular hub that integrates the environmental and hormonal signaling pathways (Choi et al., 2016, Mol. Cells 39, 587-593). PIF4 is a member of the family of PHYTOCHROME INTERACTING FACTORs (PIFs) acting negatively in the phytochrome B signaling pathway. PIF4 expression dynamics have been investigated to control adverse developmental changes occurring under high ambient temperature (Koini et al., 2009, Curr. Biol. 19, 408-413). PIF4 promoter comprises regulatory element such as a LUX Binding site (LBS) and a G-box motif that act as cis-regulatory elements. Such LBS motif is particularly targeted by the Evening Complex (EC) that coordinates environmental signals with endogenous pathways. The active form of phytochrome B, a red light photoreceptor, localises to G-box region of the PIF promoter, repressing PIF4 expression (Jung, J. H. et al. *Science* 354, 886-889, doi:10.1126/science.aaf6005 (2016).

Thus, there is a strong need to identify a way of controlling plant tolerance. The present invention seeks to meet this and other needs.

SUMMARY OF THE INVENTION

The inventors have engineered plants that are tolerant to higher ambient temperature by targeting a particular regulatory motif of the PIF4 promoter. Surprisingly, the inventors show that the inhibition the G-box motif of the PIF4 promoter leads to plant tolerance to higher ambient temperature.

The present invention relates to a genetically engineered plant wherein a G-box motif of the Phytochrome Interacting Factor 4 (PIF4) promoter is inactivated. Preferably, the G-box motif is inactivated by mutation selected from the group consisting of addition, deletion, substitution and combinations thereof, preferably by deleting the G-box motif.

In one aspect, the G-box motif is within 2 kb of the PIF4 gene start codon and/or within 1 kB of the LUX binding site of the PIF4 promoter.

In a preferred aspect, the G-box motif before the inactivation has a sequence of SEQ ID NO: 1 or a sequence having at least 80% sequence identity to SEQ ID NO: 1.

Particularly, the genetically engineered plant has a thermosensory response which is inhibited.

Preferably, the genetically engineered plant according to the invention is tolerant to an increase in ambient temperature, preferably by 2, 3, 4, 5° C. or more.

The invention also concerns a method for inhibiting the thermosensory response of a plant to an increase in ambient temperature, preferably by 2, 3, 4, 5° C. or more, comprising inactivating a G-box motif of the PIF4 promoter in said plant.

Preferably, the G-box motif in the PIF4 promoter is inactivated by deletion, preferably by deletion with a CRISPR-Cas9 system.

In one aspect, the method according to the invention comprises:
a) introducing into the plant a nucleic acid comprising a dual guide RNA which targets sequences upstream and downstream the G-box motif of the PIF4 promoter in the genome of the plant;
b) introducing into the plant a Cas9 endonuclease molecule that induces a double strand break at or near the upstream and downstream sequence of the G-box motif of the PIF4 promoter; and
c) optionally screening the plant seeds to determine if a double strand break has occurred at or near the G-box motif of the PIF4 promoter, thereby leading the G-box motif deletion; and
d) optionally recovering the plants or seeds in which the G-box motif has been deleted.

Preferably, the introducing steps comprise delivering into the plant cell a T-DNA containing a nucleic acid sequence encoding the Cas9 endonuclease and a nucleic acid sequence encoding the dual guide RNA, and wherein the delivering of the T-DNA is via *Agrobacterium*.

Particularly, the thermosensory response raised by the plant includes a developmental response selected from the group consisting of hypocotyl elongation, petiole elongation, root growth, flowering, seed number, seed size and germination.

Preferably, the plant is a crop.

In one aspect, the plant is a monocotyledonous plant, preferably selected from the group consisting of wheat, maize and rice.

In another aspect, the plant is a dicotyledonous plant preferably selected from the group consisting of tomato, soybean, tobacco, potato, rape, cabbage, broccoli, camelina and *Arabidopsis*. In a particular aspect, the plant belongs to the Brassicaceae family.

The invention finally provides a seed from the genetically engineered plant described herein.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

DETAILED DESCRIPTION

Figure 1:
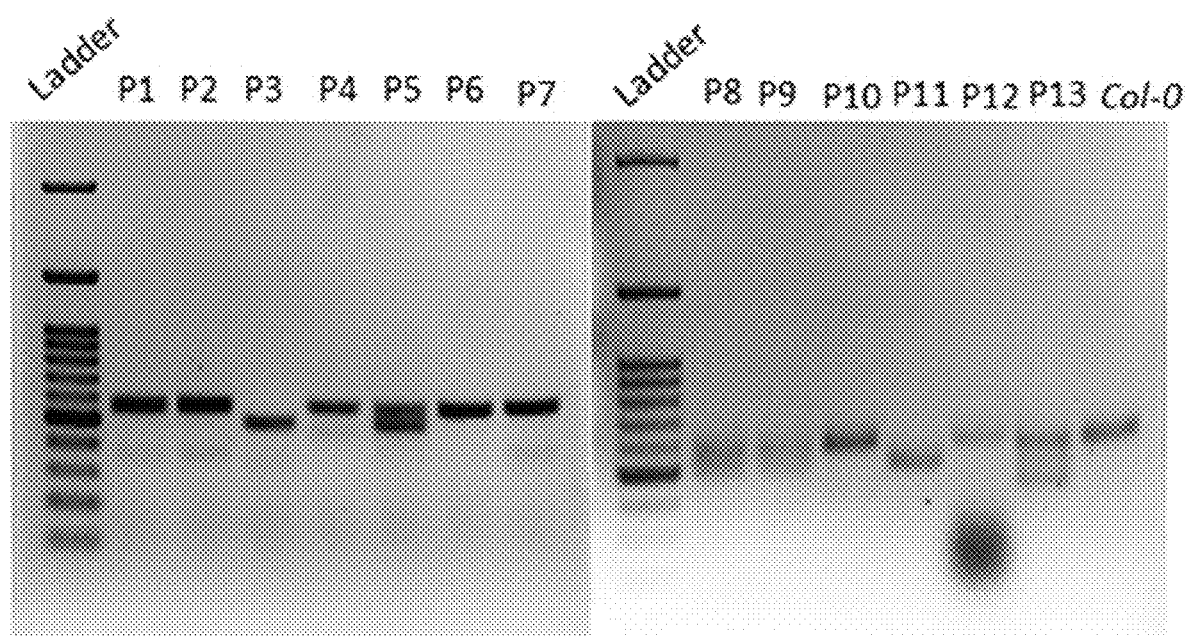
FIG. 1. PCR amplicon from PIF4 promoter of different F1 plants for genotyping. Genomic DNA from Different F1 G-Box CRISPR plants were PCR amplified with primer PGP23F and PGP23R screening for deletion of G-Box region of PIF4 Promoter. P3 and P11 are homozygous mutants for G-Box deletion while P5, P8, P9, P11 and P13 are heterozygous G-Box Crispr Mutant plants.

The inventors provide a genetically engineered plant wherein the G-box motif of the Phytochrome Interacting Factor 4 (PIF4) promoter is inactivated, thereby resulting in a plant with tolerance to an increase in ambient temperature. Surprisingly, the alteration of the G-box motif of the PIF4 promoter inhibits the thermoregulatory response of the plant under high growth permissive temperatures. It particularly slows down the thermoresponsive growth of the plant at high, but growth permissive, temperatures (i.e. temperatures before the heat stress response starts). These findings allow the improvement of plant phenotype at higher ambient temperature.

The genetically engineered plant has in particular one or several of the following advantages compared to wild type plants when the ambient temperature increases:
  they better tolerate an increase in temperature and show a phenotype similar to the phenotype observed in the optimal physiological temperature range (e.g. the hypocotyl and petiole are not submitted to elongation although this is the common mechanism observed in wild type plant under increased ambient growth temperatures);
  their flowering time period is longer and they present an increased silique size, versus the wild type plant, allowing to improve plant productivity at higher ambient temperature;
  they present an improved root phenotype versus the wild type plant that secures water resources and/or promotes biomass and/or seed/grain production at higher ambient temperature.

These characteristics are surprising as the literature suggests that binding of a transcription factor-phytochrome B complex to the G-box motif is important for the repression of PIF4 and that the binding of this complex is dependent on temperature (Jung et al., Science, 2016: Vol. 354, Issue 6314, pp. 886-889; Legris et al., Science, 2016: Vol. 354, Issue 6314, pp. 897-900).

Since the G-Box mutation occurs in the promoter, only transcription factors that bind this particular region of the promoter are not able to bind anymore, hence only the PIF4 overexpression at higher temperature may be affected by this of type mutation. Other transcription factors that do not require binding the G-box element will still regulate PIF4 expression. Moreover, since the mutation does not occurs in the protein coding region of PIF4, PIF4 protein is not mutated hence functional PIF4 can still be expressed.

Definitions

In order that the present invention may be more readily understood, certain terms are defined hereafter. Additional definitions are set forth throughout the detailed description.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art.

The term "transgenic" or "genetically engineered" or "genetically modified" refers to any cell, cell line, callus, tissue, plant part or plant, in which genetic materials (e.g. genome) has been modified using genetic engineering methods (i.e. in a way that does not occur naturally by mating and/or natural recombination), including initial transgenic events as well as those created by sexual crosses or asexual propagation from the initial transgenic event. The term "transgenic" used herein does not encompass the modification of the genome by conventional plant breeding methods or by naturally occurring events such as random cross-fertilization, non-recombinant viral infection, non-recombinant bacterial transformation, non-recombinant transposition, or spontaneous mutation. "Genetically modified plant" or "genetically engineered plant" encompasses "transgenic plants", "cisgenic plants" and "subgenic plants". Preferably, these terms include reference to a plant which comprises within its genome a modification in a nucleotide sequence, such as the sequence of a gene, a promoter or a regulatory element of a promoter. The modified sequence may results from substitution, insertion or deletion of a single or several nucleotides. Preferably, the modification is stably generated within the genome such that the modification is passed on to successive generations. "Genome" as it applies to plant cells encompasses not only chromosomal DNA found within the nucleus, but also organelle DNA found within subcellular components (e.g., mitochondria, plastid) of the plant cell.

The term "plant" includes reference to whole plant, part of a plant, plant organs, plant tissues, plant cells, seeds and progeny of the same. Plant cells include, without limitation, cells from seeds, suspension cultures, embryos, meristematic regions, callus tissues, leaves, roots, shoots, gametophytes, sporophytes, pollen, and microspores. The term "progeny" comprises any subsequent generation of a plant. A "T0 plant" is a parental plant that has been recovered from a transformation and regeneration process. Progeny of T0 plants are referred to as T1 (first progeny generation), T2 (second progeny generation), etc.

By "crop" or "crop plant" is meant any plant which is grown on a commercial scale for human or animal consumption or use and/or harvested for profit or subsistence. Crop may refer either to the harvested parts or to the harvest in a more refined state.

The terms "monocot" and "monocotyledonous plant" are used interchangeably herein and refer to a class of plants in which the seed produces only one leaves (or cotyledons). They are generally characterized by the absence of consecutive layers of wood in the stem, by the straight veins of the leaves and by the composition of the flowers which are generally multiples of three.

The terms "dicot" and "dicotyledonous plant" are used interchangeably herein are refer to a class of plants in which the seed produces two leafs. Their leaves have generally a petiole and reticulate veins and the woody forms are generally characterized by the presence of a cambium which allows the growth in width of their trunk.

The terms "wild type plant" or "wild type" or "wt" refer to the phenotype of the typical form of a plant as it generally occurs in nature or results from breeding under natural conditions. A "wild type" is conceptualized as a plant of the standard normal or more frequent phenotype, in contrast to phenotypes that may result from mutation.

As used herein, "control" or "control plant" provides a reference point for measuring changes in phenotype of a subject plant or plant cell in which genetic modification, such as transformation, has been affected as to a sequence of interest.

"Phenotype" as used herein means the detectable characteristics of a cell or organism such as plants.

As used herein, the terms "promoter" and "transcriptional promoter" are equivalent and refer to a control region of a nucleic acid sequence at which transcription initiation and rate of transcription of the remainder of a nucleic acid sequence are controlled. A promoter may also contain subregions to which regulatory proteins and molecules may bind, such as RNA polymerase and other transcription factors. A promoter drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence. A "plant promoter" is a promoter capable of initiating transcription in plant cells.

As used herein, the term "phytochrome interacting factor 4" or "PIF4" refers to a basic-helix-loop-helix (bHLH) transcription factor that functions as a negative regulator of phytochrome B signaling. PIF4 is known to be well conserved in the Plantae kingdom. Alternative names of PIF4 are Basic helix-loop-helix protein 9 (short name: AtbHLH9 or bHLH 9), Phytochrome-interacting factor 4, Short under red-light 2 (SRL2), Transcription factor EN102 and bHLH transcription factor (bHLH009). PIF4 is for example described in databases under the following accession numbers UniGene: At.19015 (*Arabidopsis thaliana*), Os.44516 (Rice) and Zm.27306 (Maize). The PIF4 protein is for example disclosed in UniProt under accession number: F4IQ51 or Q8W2F3 (*Arabidopsis*), K4F270 (Rice) and A0A1D6MR85 (Maize). PIF4 protein has been shown to bind the regulatory E-box and G-box motifs of its own promoter. Such G-box motif can be repeated in the PIF4 promoter.

As used herein, the term "G-box motif" refers to a highly conserved DNA sequence that has been identified in the 5' upstream region of plant genes exhibiting regulation by a variety of environmental signals and physiological cues. Preferably, the term "G-box motif" refers to a genetic signature which comprises a core sequence of a G-box motif, preferably consisting of the nucleotide sequence "ACGT". Particularly, such motif is comprised in the PIF4 promoter.

The terms "polynucleotide", "nucleic acid" and "nucleic acid sequence" are equivalent and refer to a polymeric form of nucleotide of any length, for example RNA or DNA. Nucleic acids (e.g., components, or portions, of the nucleic acids) of the present invention may be naturally occurring or engineered. Engineered nucleic acids include recombinant nucleic acids and synthetic nucleic acids.

By "nucleotide change" or "nucleotide modification" or "nucleotide mutation" is meant herein a change in the nucleotide sequence relative to a reference sequence. Preferably, the reference sequence is a wild-type sequence. Modification or mutation includes substitution, insertion and/or deletion in a sequence. By "substitution" herein is meant the replacement of a nucleotide at a particular position in a parent polynucleotide sequence with another nucleotide. By "insertion" is meant the addition of a nucleotide at a particular position in a parent polynucleotide sequence. By "deletion" is meant the removal of a nucleotide at a particular position in a parent polynucleotide sequence. As used herein, "nucleotide position" or "nucleotide position number" are used interchangeably and refer to the position of a particular nucleotide in a nucleotide sequence, generally specified with the one letter codes for the nucleotides (i.e. A, T, G, C). The first nucleotide in the nucleotide sequence (i.e. starting from the N terminus) should be considered as having position 1.

As used herein, the term "gene" can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

As used herein, "homology", "identity" or "similarity", when used in the context of two or more polynucleotide or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The term "percentage of identity" in relation to sequences designates the level of identity or homology between said sequences and may be determined by techniques known per se in the art. Typically, the percentage of identity between two nucleic acid sequences is determined by means of computer programs such as GAP provided in the GCG program package (Program Manual for the Wisconsin Package, Version 8, August 1996, Genetics Computer Group, 575 Science Drive, Madison, Wisconsin, USA 53711) (Needleman, S. B. and Wunsch, C. D., (1970), Journal of Molecular Biology, 48, 443-453). With settings adjusted to e.g., DNA sequences (particularly: GAP creation penalty of 5.0 and GAP extension penalty of 0.3), nucleic acid molecules may be aligned to each other using the Pileup alignment software available as part of the GCG program package. The determination of percent identity between two sequences can also be accomplished using a mathematical algorithm. One, non-limiting example of a mathematical algorithm utilized for the comparison of two sequences are those described in Current Protocols in Molecular Biology (Ausubel et al., eds. 1987) Supplement 30, section 7.7.18, Table 7.7.1. or the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al, 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present invention. To obtain gapped alignments for comparison purposes, Gapped BLAST can be utilized as described in Altschul et al, 1997, Nucleic Acids Res. 25:3389-3402. Alternatively, PSI-BLAST can be used to perform an iterated search which detects distant relationships between molecules (Id). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. The alignment and the percent homology or sequence identity can be determined using software programs known in the art, for example. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

As used herein, the term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

As used herein, the terms "nucleic acid construct", "plasmid" and "vector" are equivalent and refer to a nucleic acid molecule that serves to transfer a passenger nucleic acid sequence, such as DNA or RNA, into a host cell. A vector may comprise an origin of replication, a selectable marker, and optionally a suitable site for the insertion of a sequence or gene. A vector can be either a self-replicating extrachromosomal vector or a vector which integrates into a host genome. It can also comprise expression elements including, for example, a promoter, the correct translation initiation sequence such as a ribosomal binding site and a start codon, a termination codon, and a transcription termination sequence. A nucleic acid construct may also comprise other regulatory regions such as enhancers, silencers and boundary elements/insulators to direct the level of transcription of a given gene. There are several common types of vectors including nucleic acid constructs, bacterial virus genomes, phagemids, virus genomes, cosmids, and artificial chromosomes. The nucleic acid construct can be a vector for stable or transient expression of a gene or sequence.

As used herein, the term "inactivation" refers to the direct or indirect inhibition or decrease of the expression of the biological function of a regulatory element, gene or protein, compared to a normal or previous condition. The regulation of the genetic element can be on itself (i.e. cleavage, modifications), at the stage of transcription (i.e. using silencers or repressors), or using RNAi (e.g. siRNA, shRNA, endogenous microRNA or artificial microRNA), TALEN, Zinc Finger (ZFN), meganuclease or CRISPR/Cas strategy.

"Introduced" in the context of inserting a nucleic acid fragment (e.g., a recombinant DNA construct) into a cell, means "transfection" or "transformation" or "transduction" and includes reference to the incorporation of a nucleic acid fragment into a cell such as a plant cell, where the nucleic acid fragment may be incorporated into the genome of the cell, converted into an autonomous replicon, or transiently expressed (e.g., transfected mRNA).

"Transformation" as used herein refers to both stable transformation and transient transformation. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. "Transient transformation" refers to the introduction of a nucleic acid fragment into the nucleus, or DNA-containing organelle, of a host organism resulting in gene expression without genetically stable inheritance. A "transformed cell" is any cell into which a nucleic acid fragment (e.g., a recombinant DNA construct) has been introduced.

As used herein, "CRISPR system" or "CRISPR-Cas system" refers collectively to transcripts and other elements involved in the expression of or directing the activity of CRISPR-associated ("Cas") genes, including sequences encoding a Cas gene, a tracr (tracr-activating CRISPR) sequence, a tracr-mate sequence, a guide sequence or other sequence and transcripts from a CRISPR locus.

As used herein, "Cas endonuclease" relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell. The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

As used herein, the term "guide RNA" (gRNA) relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease and guide the insertion or deletion of nucleotide. The guide RNA can be a single molecule or a double molecule (e.g. dual guide RNA).

By "thermosensing" is meant sensing of temperature or changes in temperature by a plant. The "thermosensory response" of a plant is observed in response to changes in temperature and includes regulation of the expression of temperature dependent genes and pathways (i.e. the temperature transcriptome). The thermosensory response influences developmental processes, such as flowering, hypocotyl elongation, germination and petiole growth.

As used herein the term "ambient temperature" refers to the air temperature of an environment, particularly in which a plant naturally grows.

As used herein, the term "permissive temperature", "physiological temperature", "optimum temperature" or "normothermia" refers to a range of temperatures at which a plant has a normal, functional phenotype. Based on the range of the permissive temperature, one can define a "mean temperature" or "mean permissive temperature" (e.g. for a permissive temperature range from 20° C. to 30° C., the mean temperature is 25° C.). Based on the range of the permissive temperature, one can also define an "optimal temperature" in which a plant can grow (e.g. for *Arabidopsis thaliana*, the optimal temperature is about 22-23° C., see Seed Handling datasheet of the *Arabidopsis* Biological Resource Center). It is known in the art that the "optimal temperature" may vary during the life circle or developmental stages of the plant, such as germination, vegetative growth and fruit development.

On the contrary, a "non-permissive temperature" or "non-physiological temperature" refers to a range of temperatures at which a plant shows an altered phenotype or signs of stress. These terms particularly relate to the temperature or temperature range at which a given plant species will be adversely affected as evidenced by symptoms such as necrotic lesions, alteration of growth, early flowering, decreased photosynthesis, death etc.

The terms "increased temperature", "increased ambient growth temperature", "elevated temperature" or "high temperature" refers to temperature or temperature range that is above the "mean temperature" or the "optimal temperature" as defined above. Particularly, such "high temperature" may result of an increase of 1° C., 2° C., 3° C., 4° C., 5° C., 6° C., 7° C., 8° C., 9° C. or 10° C. with respect to the mean temperature or the optimal temperature. For instance, "high temperature" may result of an increase of 1-10° C., 2-9° C., 3-8° C., 4-7° C., 5-6° C., 2-6° C. or 3-5° C. Preferably, the increase in temperature is within the physiological temperature range.

As used herein, the terms "tolerant to an increase in temperature" or "high temperature tolerance" means that a plant shows an increased tolerance to a temperature higher than its optimal physiological temperature, compared to a wild type or control plant. Preferably, a tolerant plant show less signs of phenotypic alteration when the temperature increases in comparison with a wild type or control plant. Preferably, a tolerant plant shows a normal or unaltered phenotype when the temperature increases, in particular compared to the optimal physiological temperature or the mean permissive temperature. Even more preferably, the tolerant plant shows a better production yield in terms of biomass, fruit size and/or seeds/grain production compared to a wild type plant at the increased temperature. Differences in physical appearance, recovery and yield can be quantified and statistically analyzed using well known measurement and analysis methods.

As used herein, the terms "temperature stress" is generally defined as the increase of temperature for a certain time that causes irreversible damages in plant growth and development. Generally, high temperature induces a particular or altered phenotype in a plant, particularly signs of stress such as necrotic lesions, alteration of growth, early flowering, elongation of hypocotyl and petiole.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually.

The term "a" or "an" can refer to one of or a plurality of the elements it modifies (e.g., "a reagent" can mean one or more reagents) unless it is contextually clear either one of the elements or more than one of the elements is described.

The term "about" as used herein in connection with any and all values (including lower and upper ends of numerical ranges) means any value having an acceptable range of deviation of up to +/−10% (e.g., +/−0.5%, +/−1%, +/−1.5%, +/−2%, +/−2.5%, +/−3%, +/−3.5%, +/−4%, +/−4.5%, +/−5%, +/−5.5%, +/−6%, +/−6.5%, +/−7%, +/−7.5%, +/−8%, +/−8.5%, +/−9%, +/−9.5%). The use of the term "about" at the beginning of a string of values modifies each of the values (i.e. "about 1, 2 and 3" refers to about 1, about 2 and about 3). Further, when a listing of values is described herein (e.g. about 50%, 60%, 70%, 80%, 85% or 86%) the listing includes all intermediate and fractional values thereof (e.g., 54%, 85.4%).

G-Box Motif of the PIF4 Promoter

The invention particularly concerns a genetically engineered plant wherein a G-box motif of the Phytochrome Interacting Factor 4 (PIF4) promoter is inactivated. The wild type plant from which the genetically engineered plant is derived comprises at least one G-box motif in the PIF4 promoter.

In one embodiment, the PIF4 promoter comprises one or more G-box motifs. Preferably, all of the G-box motifs of the PIF4 promoter are inactivated in the genetically engineered plant.

In one embodiment, the G-box motif consists of 4, 5, 6, 7, 8 nucleotides, preferably 4 nucleotides, even more preferably 6 nucleotides. Preferably, the G-box motif of the PIF4 promoter comprises a core sequence consisting of the sequence 5'-ACGT-3'. Even more preferably, the G-box motif has a nucleotide sequence comprising or consisting of 5'-CACGTG-3' (SEQ ID NO: 1) or a sequence having at least 60%, 65%, 66%, 67%, 70%, 80%, 81%, 83%, 84%, 85% sequence identity with SEQ ID NO: 1. Sequences complementary to SEQ ID NO: 1 or substantially complementary are also within the scope of the invention.

In another embodiment, the G-box motif of the PIF4 promoter may comprise or consist of a functional variant of the G-box motif. A functional variant is a variant nucleic acid sequence with nucleic acid substitutions, deletions or additions that do not affect the function of the G-box motif (e.g. to be recognized and/or bound by transcription factors such as PIF4).

In a particular embodiment, the G-box motif has a sequence of SEQ ID NO: 1 with one, two or three mutations selected from the group consisting of addition, deletion or substitution. Particularly, the mutations occur at position 1 and/or 6 of SEQ ID NO: 1.

In one embodiment, the mutation occurs in the core sequence of the G-box motif and consists of the mutation of 1, 2, 3 or 4 nucleotides of the G-box motif.

Particularly, the G-box motif is in the 5' upstream region of the PIF4 gene (i.e. upstream of the PIF4 gene start codon).

In one embodiment, the G-box motif is within 2 kilobase pair (kbp) upstream of the PIF4 gene start codon. Preferably, the first nucleotide of the G-box motif is comprised in the 2 kb upstream of the PIF4 gene start codon.

Alternatively or additionally, the G-box motif is within 1 kbp of the LUX binding site (LBS) of the PIF4 promoter. Preferably, the first nucleotide of the G-box motif is comprised in the 1 kbp upstream of first nucleotide of the LBS. Even more preferably, the first nucleotide of the G-box motif is comprised in the 500 base pair (bp) upstream of first nucleotide of the LBS. Particularly, the LBS of PIF4 comprises a LUX motif comprising or consisting of the sequence 5'-GATTCG-3' (SEQ ID NO: 2) or a sequence having at least 80% sequence identity to SEQ ID NO: 2 or wherein the LBS has a sequence of SEQ ID NO: 2 with one, two or three mutations selected from the group consisting of addition, deletion or substitution.

Particularly, the inactivation of the G-box motif relates to the decrease or the inhibition of the binding of transcription factor(s) on this particular motif. This means that when the G-box motif is inactivated, the transcription factor(s) cannot recognize nor bind the G-box motif of the PIF4 promoter due to its mutation, preferably deletion.

In a particular aspect, the inactivation of the G-box motif refers to the inhibition of the binding of the PIF4 protein on the G-box motif of the PIF4 promoter.

Inactivation of the PIF4 G-Box Motif

The inactivation of the PIF4 G-box motif is carried out by introducing mutation in the G-box, the mutation being selected from the group consisting of addition, deletion, substitution and combinations thereof.

In one embodiment, the G-box motif of the PIF4 promoter in a plant is inactivated by introducing 1, 2, 3 4, 5 or 6 mutation(s) selected from the group consisting of addition, deletion, substitution and combinations thereof into the G-box motif. Preferably, the mutation occurs in the core sequence of the G-box motif. Even more preferably, the mutation targets nucleotide(s) of position 2, 3, 4 and/or 5 of SEQ ID NO: 1.

In a preferred embodiment, the inactivation corresponds to the deletion of 1, 2, 3, 4, 5 or 6 nucleotides of the PIF4 G-box motif. In a particular aspect, the inactivation is carried out by deleting the G-box motif.

Methods for Inactivation of the PIF4 G-Box Motif

The present invention relates to:
a method for preparing a genetically engineered plant, comprising inactivating the G-box motif of the PIF4 promoter in said plant;
a method for inhibiting the thermosensory response of a plant to an increase in ambient temperature, comprising inactivating the G-box motif of the PIF4 promoter in said plant; and/or
a method that modifies temperature perception of a plant, comprising inactivating the G-box motif of the PIF4 promoter in said plant.

Mutagenesis is commonly used to induce mutations in plant materials such as seeds, embryogenic callus and protoplasts. Then, selection for mutant is performed in the first generation, whereby most mutant lines may be discarded if they do not present the interesting agronomic trait (e.g. high temperature tolerance, increased biomass and/or fruit size, seed number and/or size at higher ambient growth permissive temperatures compared to the wild type plant). The mutation and the related agronomic traits are generally confirmed in the second and third generations mainly through phenotypic stability and sequencing. Finally, only the mutant lines with desirable traits are selected as a new variety or as a parent line for crossbreeding.

Applications of the methods disclosed herein include engineering changes in thermoresponse in crop plants, resulting in plants with improved traits such as greater root growth and greater seed pods size compared to wild type plants in the case of an increase in temperature, preferably at elevated physiological temperature, even more preferably at a temperature above the mean temperature of the physiological temperature range or above the optimal temperature.

The techniques for transforming a plant are well known and described in the technical and scientific literature. These techniques include transformation of plant cells by irradiation (gamma rays, X-rays, ion beam, etc.) or treatment with chemical mutagens, injection or microinjection (Griesbach (1987) Plant Sci. 50 69-77), electroporation of DNA (Fromm et al. (1985) Proc. Natl Acad Sci. USA 82:5824; Wan and Lemaux, Plant Physiol. 104 (1994), 37-48), biolistics (Klein et al. (1987) Nature 327:773), silicon carbide fiber whisker technology (Kaeppler et al., 1992), viral vector mediated approaches (Gelvin, Nature Biotechnology 23, 684-685 (2005)) and particle bombardment (Sood et al., 2011, Biologia Plantarum, 55, 1-15), fusion of cells or protoplasts (Willmitzer, L., 1993 Transgenic plants. Biotechnology, Vol. 2, 627-659), insertion of T-DNA using *Agrobacterium tumefaciens* (Fraley et al. Crit. Rev. Plant. Sci. 4, 1-46; Fromm et al., Biotechnology 8 (1990), 833-844) or *Agrobacterium rhizogenes* (Cho et al. (2000) Planta 210: 195-204) or other bacterial hosts (Brootghaerts et al. (2005) Nature 433:629-633) particularly using floral dip (Clough and Bent 1998; Zale et al. 2009).

In some aspects, the invention relates to a method to inactivate the G-box motif of the PIF4 promoter in a plant, preferably by mutation of the G-box motif, by any methods described hereabove, preferably *Agrobacterium*-mediated transformation using floral dip methods.

In a particular embodiment, the mutation of the G-box motif is performed by genome editing.

Genome Editing

In a particular aspect, the G-box motif in the PIF4 promoter is deleted by genome editing, preferably by a CRISPR-Cas system.

The Clustered Regularly Interspaced Shorts Palindromic Repeats (CRISPR)-Cas system is originally a bacterial defense system against foreign DNA. This system rests essentially on the association of a nuclease protein and a guide RNA (gRNA or sgRNA) responsible for the specificity of the cleavage site. It can be used to create DNA double-strand breaks (DSBs) at the sites targeted by the CRISPR/Cas system. This system has been used for targeted engineering of the genome in eukaryotic cells, such as plant cells (Shan Q et al., 2013, Nature Biotechnology, 31(8):686-688; Jiang W et al., 2013, Nucleic Acids Research, 41(20):e188).

In one embodiment, the CRISPR/Cas construct comprises a polynucleotide encoding a Cas enzyme, a polynucleotide encoding nuclear localization signal and at least one heterologous regulatory sequence operably linked to gRNA, wherein the gRNA is targeted to the genomic region containing the G-box motif of the PIF4 promoter. Preferably, the gRNA is targeted to the genomic region containing the polynucleotide of SEQ ID NO: 1 or a sequence having at least 80% sequence identity with SEQ ID NO: 1.

The Cas9 domain is the domain of the fusion protein that is able to interact with the guide RNA and to target the G-box of the PIF4 promoter in the genome. The Cas9 domain can consist of a Cas9 protein (also called Csn1 or Csx12), wild-type or modified, or a fragment of this protein capable of interacting with the guide RNA. The Cas9 protein can notably be modified in order to modulate its enzymatic activity. The Cas9 protein can also be truncated to remove the protein domains not essential to the functions of the fusion protein, in particular the Cas9 protein domains that are not necessary to interact with the guide RNA.

The Cas9 protein or fragment thereof as used in the present invention can be obtained from any known Cas9 protein (Makarova et al., 2008, Nat. Rev. Microbiol., 9, pp. 466-477). Exemplary Cas9 proteins that can be used in the present invention include, but are not limited to, the Cas9 proteins from *Streptococcus pyogenes, Streptococcus thermophilus, Streptococcus* sp., *Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Other Cas9 proteins that can be used in the present invention are also described in the article by Makarova et al. (Makarova et al., 2008, Nat. Rev. Microbiol., 9, pp. 466-477). Preferably, the Cas9 domain comprises, or consists of, the Cas9 protein from *Streptococcus pyogenes* (NCBI entry number: WP_010922251.1, SEQ ID NO: 8) or a fragment thereof capable of interacting with the guide RNA.

The Cas endonuclease can be introduced directly into a cell by any method known in the art, for example, but not limited to transient introduction methods, transfection and/or topical application.

In a particular aspect, the invention relates to a method as disclosed above, wherein said method comprises:
a) introducing into the plant a nucleic acid comprising a guide RNA which targets sequences upstream and downstream the G-box motif of the PIF4 promoter in the genome of the plant;
b) introducing into the plant a Cas9 endonuclease molecule that induces a double strand break at or near the upstream and downstream sequence of the G-box motif of the PIF4 promoter; and
c) optionally screening the plant seeds to determine if a double strand break has occurred at or near the G-box motif of the PIF4 promoter and;
d) optionally recovering the seeds/plants in which the G-box motif has been deleted.

In a particular embodiment, the guide RNA is a single guide or a dual guide RNA.

In one embodiment, the Cas9 endonuclease and the gRNA, preferably the dual gRNA are comprised in the same vector. The genetic transformation with a vector comprising the CRISPR/Cas9 system and the guide RNA can be achieved by any means, such as Floral Dip based transformation, biolistic transformation or electroporation of the designed construct. It can also be achieved by biolistic delivery of CRISPR/Cas9 ribonucleoproteins and in vitro gRNA transcripts.

Preferably, the introducing steps comprise delivering into the plant cell a T-DNA containing a nucleic acid sequence encoding the Cas9 endonuclease and a nucleic acid sequence encoding the dual guide RNA, and wherein the delivering of the T-DNA is via *Agrobacterium* as described hereabove.

In one embodiment, the guide RNA targets sequences in the promoter of a gene coding for PIF4, more specifically sequence flanking the G-Box motif as described herein. Preferably, the dual guide RNA targets sequences upstream and downstream of the G-box motif.

Particularly, the RNA guide is designed from the sequence of the PIF4 promoter of a crop plant, preferably a flowering plant, more preferably a plant of the Brasicaceae family, even more preferably a plant of the *Arabidopsis* genus, such as *Arabidopsis thaliana*. Thus, one aspect of the invention relates to the design of plasmid containing gRNA for deleting G-Box elements in the promoter of PIF4 for obtaining thermotolerant plants.

In one embodiment, a dual guide RNA is used to perform the inactivation of the G-box. Such dual guide comprises a first gRNA and a second gRNA.

Particularly, the first guide RNA is complementary to a sequence of 20 bp upstream of the G-box motif. Preferably, the sequence to be targeted by the first guide RNA is within the 60, 50, 40, 35, 30, 25, 24, 23, 22, 21 or 20 nucleotides upstream of the first nucleotide of the G-box motif. Even more preferably, the first nucleotide to be targeted by the first guide RNA is comprised within 60, 50, 40, 35, 30, 25, 24, 23, 22, 21 or 20 nucleotides upstream of the first nucleotide of the core sequence of the G-box motif. Alternatively, the last nucleotide of the sequence targeted by the last nucleotide of the first guide RNA is comprised within 1, 2, 3, 4, 5, 10, 20, 30 or 40 nucleotides upstream of the first nucleotide of the G-box motif. Most preferably, the first guide RNA has a sequence complementary to SEQ ID NO: 3 or to a sequence having at least 80% sequence identity to SEQ ID NO: 3.

In one embodiment, the second guide RNA is complementary to a sequence of 20 bp downstream of the G-box motif. Preferably, the sequence to be targeted by the second guide RNA is within the 100, 90, 80, 70, 60, 50, 40, 30, 20 or 10 nucleotides downstream of the last nucleotide of the G-box motif. Even more preferably, the first nucleotide of the sequence targeted by the second guide RNA is 100, 90, 80, 70, 60, 50, 40, 30, 20 or 10 nucleotides downstream of the last nucleotide of the G-box motif, preferably of the core sequence of the G-box motif. Alternatively, the last nucleotide of the sequence targeted by the second guide RNA is comprised within 100, 90, 80, 70, 60, 50, 40, 30, 20 or 10 nucleotides downstream of the first nucleotide of the G-box motif. Most preferably, the second guide RNA has a sequence complementary to SEQ ID NO: 4 or to a sequence having at least 80% sequence identity to SEQ ID NO: 4.

Accordingly, the PIF4 promoter of the plant can comprise a deletion of a sequence of 200, 190, 180, 170, 160, 150, 140, 130, 120, 110, 100, 90, 80, 70, 60 or 50 bp, such sequence comprising the G-box motif as describe herein.

Other genome-editing techniques such as designer zinc fingers (ZFN), transcription activator-like effectors (TALEs or TALEN), or homing meganucleases are also available for producing targeted genome perturbations.

Particularly, zinc finger is another type of DNA binding domain that can be used for introducing mutations into the target DNA. Zinc finger nucleases and transcription activator-like effector nucleases are artificial fusion proteins comprising an engineered DNA-binding domain fused to the nonspecific nuclease domain of the restriction enzyme Fok1 (Radek Jankele and Petr Svoboda, (2014) Brief Funct Genomics 13: 409-419; N J Palpant and D Dudzinski, (2013) Gene Therapy 20: 121-127).

Alternatively, Transcription Activator-Like Effector Nucleases (TALENs) are artificial restriction enzymes generated by fusing the TAL effector DNA binding domain to a DNA enzyme domain. TAL proteins are produced by bacteria and include a highly conserved 33-34 amino acid DNA binding domain sequence (PCT publication No. WO2014127287 US Patent Publication No. US20140087426).

Plants and Their Thermosensory Responses

It is known in the art that plants are mainly cultured under optimal temperature and conditions to reduce their stress and optimized their growth. Average range of physiological temperature has been described in the art for cereal, horticultural and legume crops (for review see Qunying Luo 2011, Climatic Change (2011) 109:583-598). For example, it is known in the art that rice is preferably grown at a physiological temperature between 25° C. and 40° C., tomato is preferably grown at a physiological temperature between 18° C. and 27° C. and *Arabidopsis thaliana* is preferably grown at a physiological temperature between 16° C. and 25° C., with an optimal temperature comprised between 22° C. and 23° C. (The Arabidopsis Biological Resource Center). When the temperature increases, plant species vary in their capacity to tolerate this change. Increase in temperature generally leads to acceleration of flowering time, greater petiole length and hypocotyl elongation and general acceleration of plant growth and development.

Here is thus provided genetically engineered plants that do not respond or are tolerant to an increase in temperature in or above the physiological range, preferably above the mean physiological temperature or the optimum temperature, wherein the G-box motif of the PIF4 promoter is inactivated. Preferably, the genetically engineered plant does not show any particular phenotype, symptom or sign of stress in response to an increase of ambient temperature. Even more preferably, the genetically engineered plants of the invention do not show a phenotype associated with elongation of hypocotyl or petiole nor early flowering under high temperature, particularly under temperatures that are at the upper limit or above the physiological range of temperature.

In one embodiment, the genetically engineered plant is tolerant to an increase in ambient temperature or to an increase of its physiological temperature compared to a wild-type plant. Preferably at elevated temperature and compared to a wild type plant, the genetically engineered plant according to the invention shows one or more of the following traits:

an increased production of leaves at the time of flowering, particularly by at least a factor of 2;
an increased silique length, particularly by at least a factor of 2;
an improved root phenotype that aides for survival at elevated ambient temperature.

Preferably, the thermotolerance of the genetically engineered plant described herein is mediated by the inactivation of the G-box motif of the PIF4 promoter according to any of the methods described hereabove. Particularly, the thermosensory responses in a plant can be altered or inhibited by any of the methods described hereabove.

In one embodiment, an increase in ambient temperature of 1° C. to 15° C., preferably of 1° C. to 10° C., more preferably of 2° C. to 5° C., even more preferably of 1° C., 2° C., 3° C., 4° C., 5° C., 6° C., 7° C., 8° C., 9° C. or 10° C., above the mean temperature or the optimal temperature, preferably inside the physiological temperature range, does not trigger a thermosensory response in the genetically engineered plant according to the invention. Preferably, an increase in ambient temperature of 1° C. to 15° C., preferably of 1° C. to 10° C., more preferably of 2° C. to 5° C., even more preferably of 1° C., 2° C., 3° C., 4° C., 5° C., 6° C., 7° C., 8° C., 9° C. or 10° C. does not lead to phenotypical changes or signs of stress in the genetically engineered plant according to the invention.

In a particular embodiment, an increase in ambient temperature of 1° C. to 15° C., preferably of 1° C. to 10° C., more preferably of 2° C. to 5° C., even more preferably of 1° C., 2° C., 3° C., 4° C., 5° C., 6° C., 7° C., 8° C., 9° C. or 10° C., above the mean temperature or the optimum temperature, preferably inside the physiological temperature range, does not lead to decreased biomass, shorter time to flowering, decreased seed production, decreased seed/grain size/volume, decreased size/volume/number of fruits.

The invention encompasses any plant comprising the PIF4 promoter and/or gene or a homologous to PIF4 promoter and/or gene that has one or more G-box elements in its promoter region, preferentially said G-box element or elements are within 2 kB of the PIF4 start codon, more preferentially 1 kb and most preferentially within 500 bp of a LUX binding site as described hereabove.

In one embodiment, the present invention contemplates a plant wherein the mutation of the G-box motif is present in a homozygous state. In another embodiment, the plant is heterozygous for the G-box mutation.

Preferably, the plant according to the different aspects of the invention is a crop. Crop according to the invention include cereal crops, such as wheat, rice, barley, maize, oat, sorghum, rye, onion, leek, millet, yam, buckwheat, turf grass, Italian rye grass, sugarcane or *Festuca* species; biofuel and bioenergy crops such as rape/canola, linseed, lupine and willow, poplar, poplar hybrids, *Miscanthus* or gymnosperms, such as loblolly pine; crops for silage (maize), grazing or fodder (grasses, clover, alfalfa), fibers (e.g. cotton, flax), building materials (e.g. pine, oak), pulping (e.g. poplar), feeder stocks for the chemical industry (e.g. acid oil seed rape, linseed), and ornamental crops such as snapdragon, petunia, roses, violets, Begonias, chrysanthemums and geraniums. Preferably, the plant may be selected from group consisting of lettuce, sunflower, *Arabidopsis*, broccoli, spinach, water melon, squash, cabbage, tomato, camelina, potato, yam, capsicum, tobacco, cotton, okra, apple, rose, strawberry, alfalfa, bean, soybean, field (fava) bean, pea, lentil, peanut, chickpea, apricots, pears, peach, grape vine or citrus species.

The genetically engineered plant may be a monocot or a dicot.

In one aspect, the plant belongs to the clade of dicots. Examples of plants from the dicots clade include, but are not limited to, the Solanaceae family, comprising *Solanum lycopersicum* (tomato), *Solanum tuberosum* (potatoes), *Solanum melongena* (eggplant), *Capsicum* genus (pepper) and *Nicotiana tabacum* (tobacco); the Vitaceae family comprising the *Vitis* genus (grapevines); the Brassicaceae family, comprising *Brassica rapa* (turnip and chines cabbage), *Camelina sativa*, mustard species and *Arabidospis thaliana*, and the Rosacceae family, comprising *Malus pumila* (apple) and *Pyrus* species (pear). In a particularly preferred aspect, the dicot plant is *A. thaliana*.

In another aspect, the plant belongs to the clade of monocots. An example of plants from the monocot clade includes, but is not limited to, the Arecaceaef, Amaryllidaceae or Poaceae family. A preferred example of plant from the monocots clade, belonging to the Poaceae family is *Zea mays* (maize).

In one aspect, the invention also provides progeny and/or seeds from the genetically engineered plant according to the invention.

Progeny includes subsequent generations obtained by self-pollination or out-crossing of a plant. Progeny also includes hybrids and inbreeds.

In one embodiment, seeds are obtained from the genetically modified plants according to the invention. These seeds can be grown to produce plants that would exhibit a tolerance to high temperature, or used in a breeding program to produce hybrid seed, which can be grown to produce plants that would exhibit such characteristic. The seeds may also be used for testing stability and inheritance. Generally, two or more generations are cultivated to ensure that the phenotypic feature is stably maintained and transmitted. Preferably, seeds derived from mature genetically modified plants that are homozygous.

EXAMPLES

The following Figures and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Genotyping Positive Plants for the G-Box CRISPR Plants.

For genotyping positive plants for the G-Box CRISPR plants we used the following primers.

| Serial No. | Name | Sequence | SEQ ID NO: |
|---|---|---|---|
| PGP23F | PIF4 G-Box Genotype FR | 5'-TCAGAGTTTTTTA GATAAGG-3' | 5 |
| PGP23R | PIF4 G-box Genotype RV | 5'-GCAAGTCCATGAGT CCGTTC-3' | 6 |

Figure 3:
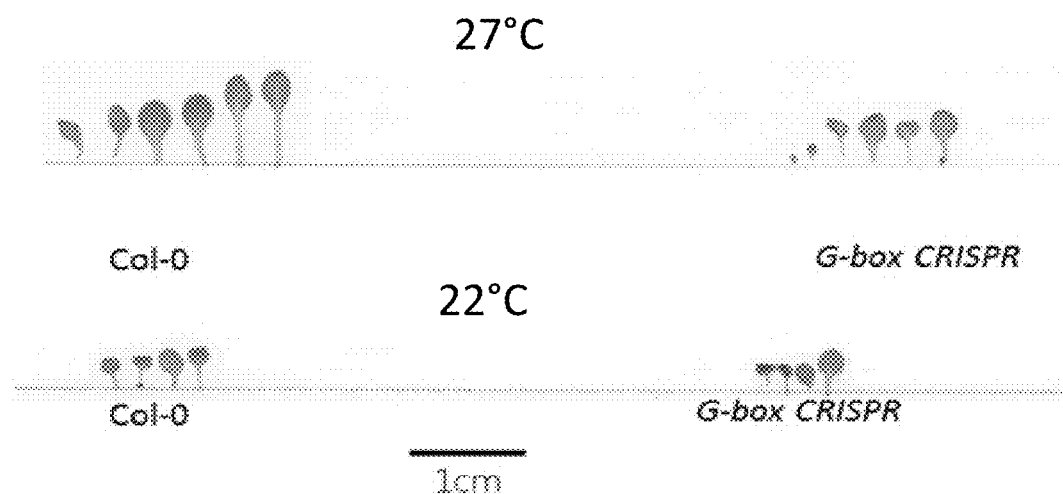
FIG. 3. Petiole elongation in G-Box CRISPR plants compared with Col-0. Col-0 plants have bigger petioles at 22° C. or at 27° C. compared to G-Box CRISPR Plants. The petioles images are representative of petioles collected from whole plants in 6 leaves stage grown at 27° C. and 4 leaves stage for plants grown at 22° C.

Genomic DNA was isolated from several plants that were fluorescence positive. The PIF4 promoter was screened using PGP23F and PGP23R primers from the genomic DNA using PCR. From the PCR amplicons it was found that P3, P11 are homozygous G-Box deletion mutants while P5, P8, P9 are heterozygous mutants for G-Box deletion (FIG. 3).

Hypocotyl Elongation of G-Box CRISPR Mutants

Figure 2:
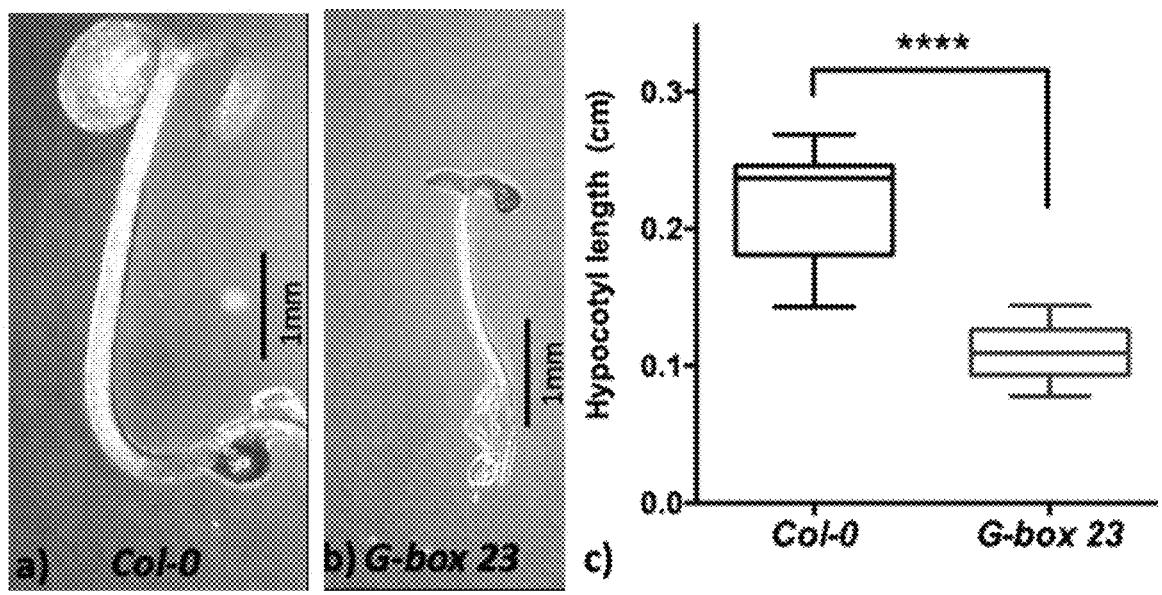
FIG. 2. Hypocotyl phenotype of G-Box CRISPR plants compared to Wildtype Col-0 plants. A. Representative hypocotyl images of Col-0 and G-Box CRISPR mutant plants. B. Hypocotyl length of 15 plants each for Col-0 and G-Box CRISPR were measured and average hypocotyl length is plotted.

Plants respond to increase in ambient temperature by hypocotyl elongation. Hence G-Box CRISPR mutant seeds were germinated at 27° C. along with Col-0 plants to check for hypocotyl elongation. From the hypocotyl elongation experiments it was found that at 27° C. the G-Box CRISPR mutant had smaller hypocotyls compared to Col-0 plants. While the average hypocotyl length of Col-0 Plants were 2.15 mm, the average hypocotyl lengths of G-Box CRISPR plants were found to be 1.08 mm. Hence the inventors conclude that hypocotyl elongation due to higher ambient temperature is compensated with the G-Box CRISPR mutation. (FIG. 2)

Petiole Elongation Response of G-Box CRISPR Mutants

The normal response of wildtype Col-0 plants to higher temperature is to increase petiole length. This response balances the risk of heat damage versus water shortage. The risk of heat related damage can be averted through evaporation via the stomata and requires water availability for optimum efficacy. The majority of water is lost through transpiration. Longer petioles lead to fewer stomata at higher temperature to control the rate of transpiration and minimize water loss. However, the architectural changes in the leaf help compensate for the reduced number of stomata to allow for cooling.

For the G-Box mutants and wildtype plants grown at 22° C. little difference was observed in petiole length. However for the plants grown in 27° C. keeping all conditions identical, it was observed that G-box CRISPR plants showed smaller elongation in petiole length compared to Col-0 plants (FIG. 3). The phenotype of these plants was similar to those seen at 22° C. for the wildtype plants.

Flowering Time Response of G-Box CRISPR Plants

Figure 4:
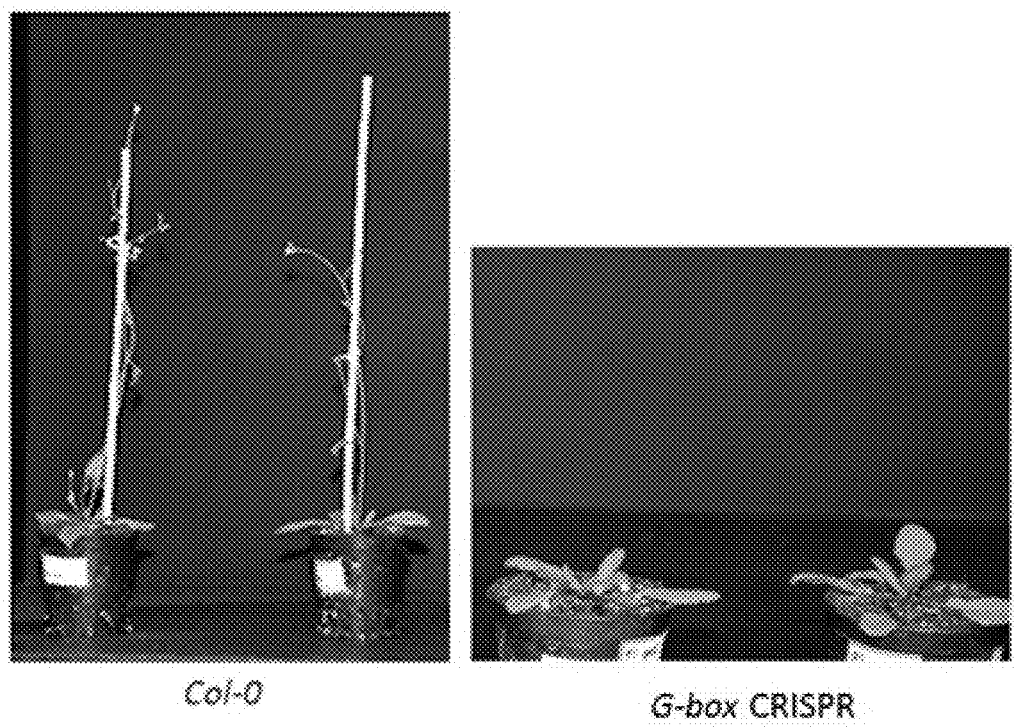
FIG. 4. Flowering phenotype of Col-0 plants compared to G-Box CRISPR mutant plants grown at 27° C. Col-0 and G-Box CRISPR plants were grown in Long day condition (16 h light and 8 h dark) at 27° C.

Flowering is also linked to temperature. It's known that at 27° C. *Arabidopsis* flowers earlier than at 22° C. (Capovilla et al., 2015). Hence G-box mutants and wildtype plants were grown at 27° C. The inventors show that with the G-Box mutation, the plants are able to flower later than the wildtype type plants at 27° C. (FIG. 4). It was observed that while Col-0 plants flowered at 7~8 rosette leaves, the G-Box mutants flowered much later at 12~14 rosette leaves, similar to wildtype plants grown at 22° C. under long day conditions (16 hour light, 8 hour dark).

G-Box CRISPR Plants Have Larger Seed Pods at Higher Ambient Temperature.

Figure 5:
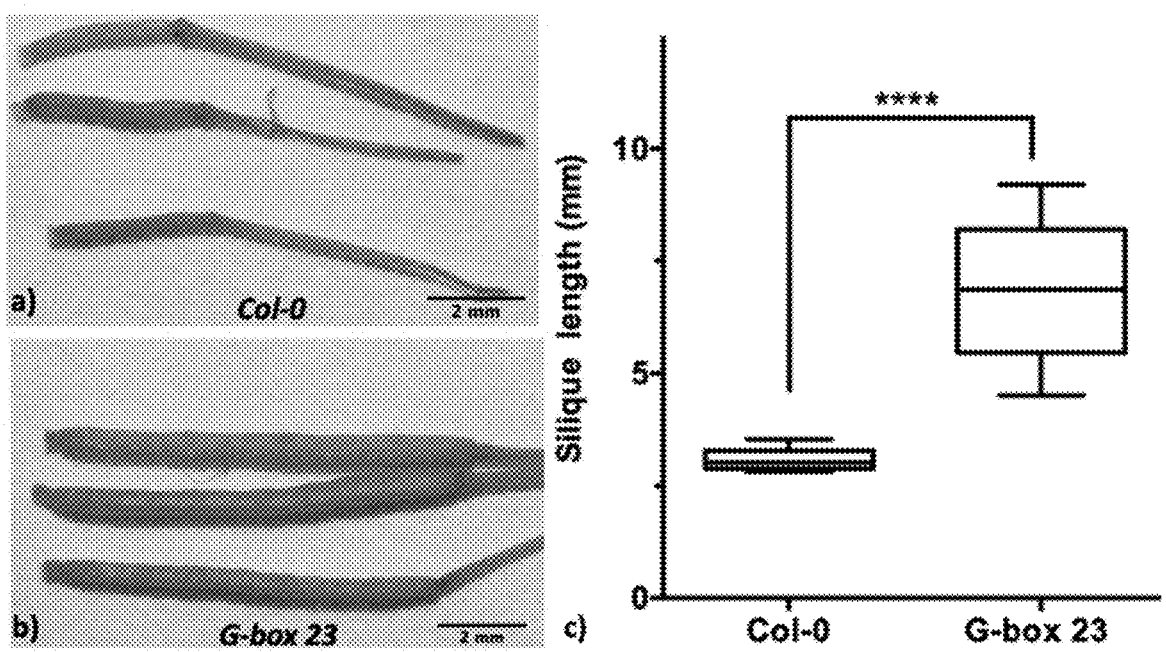
FIG. 5. Silique Phenotype of G-Box CRISPR Plants compared to Col-0 wt grown at 27° C. Silique from Col-0 plants (a) grown at 27° C. compared with siliques from G-Box CRISPR plants (b) and c) comparison between silique lengths of Col-0 plants and G-Box CRISPR plants.

Plant productivity depends upon seeds produced hence it's linked to the size and number of siliques produced. The silique length of G-box mutants and wildtype plants at 27° C. were observed to see if there was any difference in the silique lengths. It was found that silique length of Col-0 plants were 3.3 mm while the G-Box mutant had a silique length of 6.7 mm (FIG. 5).

G-Box CRISPR Plants Have Longer Roots and More Secondary Roots.

Figure 6:
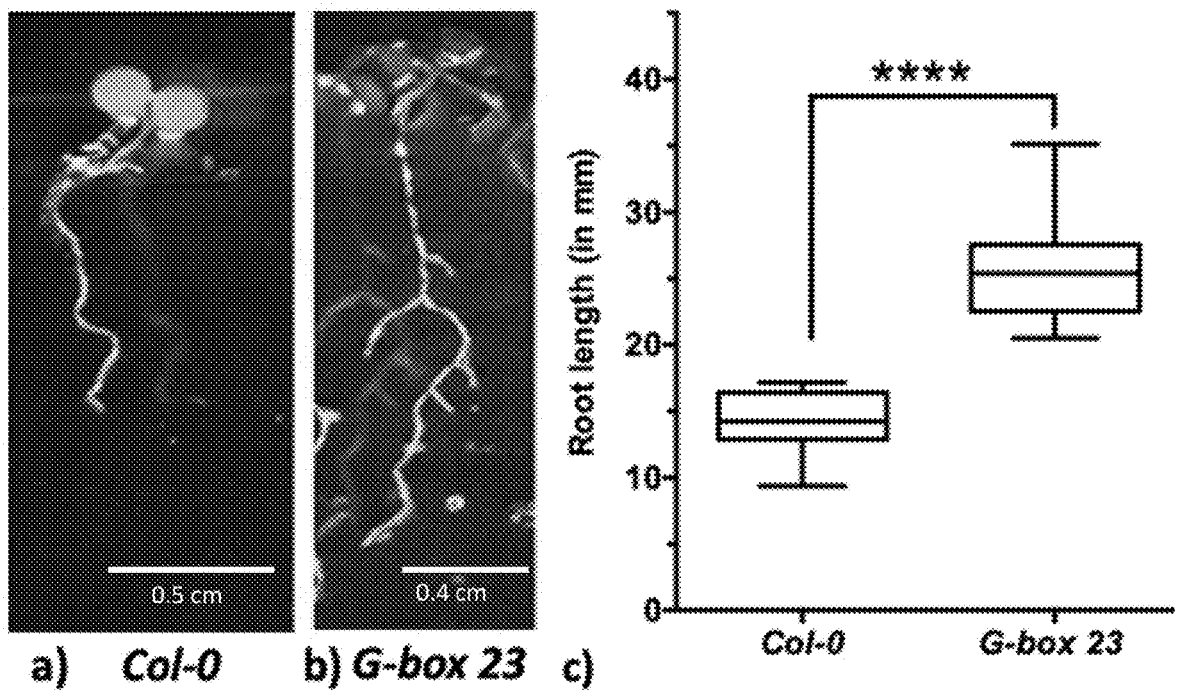
FIG. 6. Root phenotype of Col-0 plants compared with G-Box CRISPR plants. Roots from Col-0 plants grown at 27° C. compared with roots from G-Box CRISPR plants.

For plants to survive in higher ambient temperature, it's important that they can secure water resources for growth and for cooling through transpiration. Having a longer primary root and more lateral roots helps to efficiently uptake water. This is likely to be an important trait when growing under higher ambient temperature. It was found that compared to wildtype plants the G-Box mutants had longer primary roots and more lateral roots emerging. Average root length of 12 days old Col-0 wt. plants was 1.33 cm compared to 2.66 cms for the G-Box mutants. Also it was observed that the G-box mutants had larger number of lateral roots emerging compared to Col-0 wildtype plants (FIG. 6).

Material and Methods

Plasmid Construct

The system is designed to use CRISPR Cas9 for modifying plants and use GFP based selection for selecting positive seeds from the plants transformed with the vector. The system facilitates use of multiple gRNA's. The whole system is a two vector system comprising of a guide RNA vector for multiple guide assembly and the final Ccas9 vector comprising of the eGFP and Cas9. Multiple gRNA's are assembled on the gRNA vector and then the whole gRNA cassette is excised and cloned into the pGreenCRISPR vector. Later this final vector is transformed with the floral dip method. Seeds from the plants transformed with the final vector are selected for GFP signals and the positive seeds carry the CRISPR Cas9 system intended.

1000 base pairs (bp) upstream of the PIF4 transcription start site (TSS) was selected to search for the G-Boxes (CACGTG). One G-Box was located 655 bases upstream of PIF4 TSS. Sequence flanking 200 bp upstream and downstream of this G-box was processed through the CHOPCHOP server (chopchop.cbu.uib.no/) for locating probable gRNA spacers with minimal off-target effects.

Spacers with a score under 20 were selected as suggested by the program (scores above 20 suggest that there might be off site targets apart from the desired targets). Following specific over-hangs were added on the primers for ligation:

Protospacer sequences used for G-box Guide RNA are as follows.

| Name | Sequence | SEQ ID NO: |
|---|---|---|
| G-box CRISPR 2 FR | GATTGCATAAAGATATTACAGCGA | 7 |
| G-box CRISPR 2 RV | AAACTCGCTGTAATATCTTTATGC | 8 |
| G-box CRISPR 3 FR | GATTCAAGTTCTGGGACATTGTGT | 9 |
| G-box CRISPR 3 RV | AAACACACAATGTCCCAGAACTTG | 10 |

Cloning Procedure

Protospacers mentioned were synthesized at Eurofins genomics. The forward and reverse protospacers were annealed using 10× annealing buffer (1 mL of 1M Tris pH 7.5 (100 mM)).

The reaction mix was incubated 3-4 minutes at 95° C. and was let to cool down slowly in the heating block over-night.

For obtaining G-Box gRNAs, the double stranded protospacers were ligated into the pAtU6-26:gRNA plasmid. The ligated plasmids were transformed in competent bacteria to obtain the gRNA constructs. The inventor chose to use dual guides based gRNA constructs for targeting G-Box.

The cassette containing the guide(s) RNA(s) from pBSK:AtU6-26:gRNA were finally cloned into pGreenCRISPR vector containing Cas9 and the AtS2:eGFP sequence. Following protocol was followed for restriction digestion.

The digestion products were analyzed on a 1% agarose gel, the bands were excised and purified using QIAquick gel extraction and PCR cleanup kit from Qiagen®. Fragments obtained were ligated overnight using T4 DNA ligase and transformed in competent bacteria. Bacteria were grown in LB Agar plates containing kanamycin for selection of positive transformants.

Genetic Transformation of Plants With the pGreenCRISPR Vector

Genetic transformation was performed by introducing constructs into *Agrobacterium tumefaciens* strain GV3101, which was then used to transform wildtype plants using floral dip method (Clough and Bent, 1998).

Genotyping of Mutants.

Singles leaves were harvested from 20 days old plant. Leaves were frozen in liquid nitrogen. The leaves were disrupted in a TissueRuptor II homogenizer using glass beads. DNA was extracted from these samples using CTAB DNA extraction method (Richards et al., 1994). To verify if the plants were homozygous or heterozygous for the deletion of G-Box deletion, PCR was performed using primers flanking the expected deletion sites. Primers used for this purpose are as following.

| PIF4 Promoter Genotype FR | 5'-TCAGAGTTTTTTTAGATAAG G-3' | SEQ. ID NO: 5 |
|---|---|---|
| PIF4 Promoter Genotype RV | 5'-GCAAGTCCATGAGTCCGTT C-3' | SEQ. ID NO: 6 |

All PCR products were resolved on a 1.5% agarose gel containing GelRed® to view amplicons.

Expected amplicon size from wildtype plants is 586 bp. The deletion results in removal of 102 bp from the amplicon hence if deletion is present the amplicon size is supposed to be 484 bp. It's possible that plant might be homozygous or heterozygous for the deletion. Hence heterozygous plants produce two amplicons, one pertaining to 586 bp and the other pertaining 484 bp. The homozygous mutants produce one amplicon of 484 bp.

Phenotyping of Mutants.

Col-0 (wild type plants) and mutant plants were grown in soil, in long day (LD) chambers at 22° C. for 10 days and were then transferred to 27° C. to score leaf, silique size and flowering time phenotypes.

RNA Isolation and Quantitative PCR

Plants were grown in LD for 10 days in MS Media and samples were harvested in an interval of 4 hours starting on light switching in Percival cabinets. 4-6 seedlings were harvested for each line at each time point. Total RNA was extracted using RNeasy Plant mini kit (Qiagen) according to manufacturer's instructions. Total RNA (1 μg) was treated with DNaseI (NEB). For qRT-PCR, cDNA was generated synthesized from 1 μg of DNaseI treated RNA using iScript™ cDNA synthesis kit (Bio-Rad, 1708891) using manufacturer's protocol. Expression of PIF4 in different plant lines were determined through PCR with ACTIN used as a control. qRT-PCR measurements were performed in a Bio-Rad CFX384™ Real-Time system with SsoFast™ EvaGreen® Supermix (Bio-Rad). Quantification was performed with the relative −ΔΔCt method, using ACTIN for normalization. All quantification and statistical analysis were performed using CFX Maestro™ software (Bio-Rad).

The invention claimed is:

1. A genetically engineered plant wherein a G-box motif of the Phytochrome Interacting Factor 4 (PIF4) promoter is inactivated, wherein the G-box motif has a core sequence consisting of the nucleic acid sequence of SEQ ID NO: 1 before inactivation and is within 1 kb of the LUX binding site of the PIF4 promoter and within 2 kilobases (kb) of the PIF4 gene start codon, wherein the LUX binding site has a core sequence consisting of the nucleic acid sequence of SEQ ID NO: 2; wherein the inactivation of the G-box motif leads to the decrease or inhibition of the binding of the PIF4 protein on the G-box motif of the PIF4 promoter, wherein the plant has a thermosensory response which is inhibited so that the plant is tolerant to an increase in ambient temperature, and wherein the genetically engineered plant is from the family Brassicaceae.

2. The genetically engineered plant of claim 1, wherein the G-box motif is inactivated by mutation selected from the group consisting of addition, deletion, substitution and combinations thereof.

3. The genetically engineered plant of claim 1, wherein the G-box motif is within 1 kilobase (kb) of the PIF4 gene start codon.

4. The genetically engineered plant of claim 1, wherein said thermosensory response comprises a developmental response selected from the group consisting of hypocotyl elongation, petiole elongation, root growth, flowering time, seed number, seed size and germination time.

5. A method for inhibiting the thermosensory response of a plant to an increase in ambient temperature comprising inactivating a G-box motif of the PIF4 promoter in said plant, wherein the G-box motif has a core sequence consisting of the nucleic acid sequence of SEQ ID NO: 1 before inactivation and is within 1 kb of the LUX binding site of the PIF4 promoter and within 2 kilobases (kb) of the PIF4 gene start codon; wherein the LUX binding site has a core sequence consisting of the nucleic acid sequence of SEQ ID NO: 2; wherein the inactivation of the G-box motif leads to the decrease or inhibition of the binding of the PIF4 protein on the G-box motif of the PIF4 promoter, thereby inhibiting the thermosensory response of a plant to an increase in ambient temperature, wherein the plant is from the family Brassicaceae.

6. The method of claim 5, wherein the G-box motif in the PIF4 promoter is inactivated by deletion.

7. The method of claim 6, wherein inactivation of the G-box motif comprises:
 a) introducing into the plant a nucleic acid comprising a dual guide RNA which targets sequences upstream and downstream the G-box motif of the PIF4 promoter in the genome of the plant;
 b) introducing into the plant a Cas9 endonuclease molecule that induces a double strand break at or near the upstream and downstream sequence of the G-box motif of the PIF4 promoter; and
 c) optionally screening the plant seeds to determine if a double strand break has occurred at or near the G-box motif of the PIF4 promoter, thereby leading to the G-box motif deletion; and
 d) optionally recovering the plants or seeds in which the G-box motif has been deleted.

8. The method of claim 7, wherein the introducing steps comprise delivering into the plant cell a T-DNA containing a nucleic acid sequence encoding the Cas9 endonuclease and a nucleic acid sequence encoding the dual guide RNA, and wherein the delivering of the T-DNA is via *Agrobacterium*.

9. The method of claim 5, wherein said thermosensory response comprises a developmental response selected from the group consisting of hypocotyl elongation, petiole elongation, root growth, flowering time, seed number, seed size and germination time.

10. The method of claim 5, said method further comprising the recovery of seed from a plant comprising an inactivated a G-box motif of the PIF4 promoter.

11. A seed from the genetically engineered plant of claim 1, wherein the inactivated G-box motif of the PIF4 promoter in the genetically engineered plant is present in a homozygous state.

12. The genetically engineered plant of claim 1, wherein the G-box motif is inactivated by the deletion of the G-box motif.

13. The genetically engineered plant of claim 1, wherein the plant is tolerant to an increase in ambient temperature of 2° C. to 5° C. and the plant does not demonstrate phenotypical changes or signs of stress.

14. The method of claim 5, wherein the G-box motif is within 1 kilobase (kb) of the PIF4 gene start codon.

15. The method of claim 5, wherein the plant is *Brassica rapa* or *Arabidospis thaliana*.

16. The method of claim 5, wherein the plant is selected from the group consisting of rape, broccoli, cabbage, mustard, and *Arabidopsis*.

17. The method of claim 5, wherein the plant is *Arabidospis thaliana*.

* * * * *

SEQUENCE LISTING

```
<160> NUMBER OF SEQ ID NOS: 10

<210> SEQ ID NO 1
<211> LENGTH: 6
<212> TYPE: DNA
<213> ORGANISM: Artificial Sequence
<220> FEATURE:
<223> OTHER INFORMATION: G-box

<400> SEQUENCE: 1 cacgtg                                                                6

<210> SEQ ID NO 2
<211> LENGTH: 6
<212> TYPE: DNA
<213> ORGANISM: Artificial Sequence
<220> FEATURE:
<223> OTHER INFORMATION: LUX

<400> SEQUENCE: 2 gattcg                                                                6

<210> SEQ ID NO 3
<211> LENGTH: 20
<212> TYPE: DNA
<213> ORGANISM: Artificial Sequence
<220> FEATURE:
<223> OTHER INFORMATION: PIF4 target sequence 1

<400> SEQUENCE: 3
acacaatgtc ccagaacttg                                                20

<210> SEQ ID NO 4
<211> LENGTH: 20
<212> TYPE: DNA
<213> ORGANISM: Artificial Sequence
<220> FEATURE:
<223> OTHER INFORMATION: PIF4 targeted sequence 2

<400> SEQUENCE: 4
tcgctgtaat atctttatgc                                                20

<210> SEQ ID NO 5
<211> LENGTH: 21
<212> TYPE: DNA
<213> ORGANISM: Artificial Sequence
<220> FEATURE:
<223> OTHER INFORMATION: PIF4 G-Box Genotype FR

<400> SEQUENCE: 5
tcagagtttt tttagataag g                                              21
```

```
<210> SEQ ID NO 6
<211> LENGTH: 20
<212> TYPE: DNA
<213> ORGANISM: Artificial Sequence
<220> FEATURE:
<223> OTHER INFORMATION: PIF4 G-box Genotype RV

<400> SEQUENCE: 6
gcaagtccat gagtccgttc                                               20

<210> SEQ ID NO 7
<211> LENGTH: 24
<212> TYPE: DNA
<213> ORGANISM: Artificial Sequence
<220> FEATURE:
<223> OTHER INFORMATION: G-box CRISPR 2 FR

<400> SEQUENCE: 7
gattgcataa agatattaca gcga                                          24

<210> SEQ ID NO 8
<211> LENGTH: 24
<212> TYPE: DNA
<213> ORGANISM: Artificial Sequence
<220> FEATURE:
<223> OTHER INFORMATION: G-box CRISPR 2 RV

<400> SEQUENCE: 8
aaactcgctg taatatcttt atgc                                          24

<210> SEQ ID NO 9
<211> LENGTH: 24
<212> TYPE: DNA
<213> ORGANISM: Artificial Sequence
<220> FEATURE:
<223> OTHER INFORMATION: G-box CRISPR 3 FR

<400> SEQUENCE: 9
gattcaagtt ctgggacatt gtgt                                          24

<210> SEQ ID NO 10
<211> LENGTH: 24
<212> TYPE: DNA
<213> ORGANISM: Artificial Sequence
<220> FEATURE:
<223> OTHER INFORMATION: G-box CRISPR 3 RV

<400> SEQUENCE: 10
aaacacacaa tgtcccagaa cttg                                          24
```